US009048435B2

(12) United States Patent
Werner et al.

(10) Patent No.: US 9,048,435 B2
(45) Date of Patent: Jun. 2, 2015

(54) ORGANIC SEMICONDUCTING MATERIALS AND ORGANIC COMPONENT

(75) Inventors: Ansgar Werner, Dresden (DE); Sascha Dorok, Dresden (DE); Carsten Rothe, Dresden (DE); Andreas Haldi, Dresden (DE); Michael Felicetti, Halle (DE); Volker Lischewski, Bitterfeld-Wolfen OT Reuden (DE); Mirko Tschunarjew, Raguhn (DE)

(73) Assignees: Novaled AG, Dresden (DE); Sensient Imaging Technologies GmbH, Wolfen (DE)

( * ) Notice: Subject to any disclaimer, the term of this patent is extended or adjusted under 35 U.S.C. 154(b) by 594 days.

(21) Appl. No.: 13/402,142

(22) Filed: Feb. 22, 2012

(65) Prior Publication Data

US 2012/0223296 A1    Sep. 6, 2012

(30) Foreign Application Priority Data

Mar. 1, 2011    (EP) .................................... 11156346

(51) Int. Cl.
| | | |
|---|---|---|
| *H01L 31/00* | (2006.01) | |
| *H01L 51/00* | (2006.01) | |
| *C07C 211/58* | (2006.01) | |
| *H01L 51/42* | (2006.01) | |
| *H01L 51/50* | (2006.01) | |

(52) U.S. Cl.
CPC ............ *H01L 51/006* (2013.01); *H01L 51/4253* (2013.01); *H01L 51/506* (2013.01); *H01L 51/5088* (2013.01); *Y02E 10/549* (2013.01); *C07C 211/58* (2013.01)

(58) Field of Classification Search
CPC ............ H01L 51/0032; H01L 51/0061; H01L 51/0059; H01L 31/00; H01L 51/54; H01L 51/00; H01L 51/46; B32B 27/18
USPC .............. 252/519.21, 500; 313/504; 558/434, 558/430; 546/330; 257/40, E51.012, 257/E51.018, E51.026; 428/500; 136/263
See application file for complete search history.

(56) References Cited

U.S. PATENT DOCUMENTS

| | | | |
|---|---|---|---|
| 6,908,783 | B1 | 6/2005 | Kuehl et al. |
| 7,074,500 | B2 | 7/2006 | Pfeiffer et al. |
| 7,274,141 | B2 | 9/2007 | Leo et al. |
| 7,355,197 | B2 | 4/2008 | Blochwitz-Nimoth et al. |
| 7,675,057 | B2 | 3/2010 | Drechsel et al. |
| 7,968,215 | B2 * | 6/2011 | Begley et al. ............... 428/690 |
| 7,981,324 | B2 | 7/2011 | Hartmann et al. |
| 2006/0033115 | A1 | 2/2006 | Blochwitz et al. |
| 2007/0090371 | A1 | 4/2007 | Drechsel et al. |
| 2007/0296331 | A1 * | 12/2007 | Yabunouchi et al. ......... 313/504 |
| 2008/0265216 | A1 * | 10/2008 | Hartmann et al. ............ 252/500 |
| 2008/0311425 | A1 * | 12/2008 | Okuda et al. ................. 428/690 |
| 2009/0051271 | A1 | 2/2009 | Birnstock et al. |
| 2009/0066239 | A1 * | 3/2009 | Yabunouchi .................. 313/504 |
| 2009/0235971 | A1 | 9/2009 | Pfeiffer et al. |
| 2011/0156059 | A1 * | 6/2011 | Reineke et al. ............... 257/79 |
| 2011/0240963 | A1 * | 10/2011 | Jou et al. ........................ 257/40 |
| 2011/0303902 | A1 * | 12/2011 | Jou et al. ........................ 257/40 |
| 2012/0121933 | A1 * | 5/2012 | Ma et al. ....................... 428/704 |

FOREIGN PATENT DOCUMENTS

| | | | |
|---|---|---|---|
| WO | WO 2006011880 A1 * | 2/2006 | |
| WO | WO 2008131750 A2 * | 11/2008 | ............. H01L 51/50 |
| WO | WO 2011131185 A1 * | 10/2011 | |

OTHER PUBLICATIONS

Gregor Schwartz et al., "Reduced efficiency roll-off in high-efficiency hybrid white organic light-emitting diodes", Applied Physics Letters, 92 (2008), 053311, 1-3.*
Thomas C. Rosenow et al., "Highly efficient white organic light-emitting diodes based on fluorescent blue emitters", Journal of Applied Physics, 108 (2010), 113113, 1-5.*
Benvenho et al., 2005, "Efficient Organic Light-Emitting Diodes with Fluorine-Doped Tin-Oxide Anode and Electrochemically Synthesized Sulfonated Polyaniline as Hole Transport Layer," Brazilian Journal of Physics, 35 (4A):1016-1019.

* cited by examiner

*Primary Examiner* — Douglas Mc Ginty
(74) *Attorney, Agent, or Firm* — Sutherland Asbill & Brennan LLP

(57) ABSTRACT

An organic semiconductive material comprising at least one matrix material and at least one doping material, wherein the doping material is selected from an organic compound and wherein the matrix material is selected from an diamine compound, also an organic component and a mixture for producing a doped semiconductor layer.

16 Claims, 4 Drawing Sheets

US 9,048,435 B2

ORGANIC SEMICONDUCTING MATERIALS AND ORGANIC COMPONENT

CROSS-REFERENCE TO RELATED APPLICATIONS

This application hereby claims priority to European Patent Application No. 11 156 346.6, filed 1 Mar. 2011, the disclosure of which is expressly incorporated herein by reference.

FIELD OF THE INVENTION

The present invention relates to an organic semiconductive material comprising at least one matrix material and at least one dopant, and an organic component containing this organic semiconductive material.

BACKGROUND OF THE INVENTION

It has been known for several years that organic semiconductors can be modified extensively in terms of their electrical conductivity by doping (electrical doping). Organic semiconductive matrix materials of such kind can be constructed either from compounds with relatively good electron donor properties or from compounds with relatively good electron acceptor properties. Strong electron acceptors such as tetracyanoquino-dimethane (TCNQ) or 2,3,5,6-tetrafluoro-tetracyano-1,4-benzoquinonedimethane (F4TCNQ) have become known to be effective in doping electron donor materials (HT) (U.S. Pat. No. 7,074,500). By electron transfer processes, these substances generate "holes" in electron donor type base materials (hole transporter materials), and the conductivity of the base material is modified to a greater or lesser degree depending on the number and mobility of these holes. Known examples of matrix materials with hole transporter properties include N,N'-perarylated benzidines (TPD) or N,N',N''-perarylated starburst compounds such as the substance TDATA, or also certain metal phthalocyanines, such as in particular zinc phthalocyanine ZnPc.

However, the previously described compounds have disadvantages for a technical use in the production of doped semiconductive organic layers or of corresponding electronic components with such doped layers since the manufacturing processes in large-scale production plants or those on a technical scale cannot always be controlled with sufficient precision, which results in high control- and regulating expense within the processes for achieving a desired product quality or in undesired tolerances of the products. Furthermore, there are disadvantages in the use of previously known organic acceptors with regard to electronic components such as light-emitting diodes (OLEDs), field effect transistors (FET) or solar cells since the cited production difficulties in the handling of the doping agents can lead to undesired irregularities in the electronic components or undesired ageing effects of the electronic components. However, it should be noted at the same time that the doping agents to be used have extremely high electron affinities (reduction potential) and other properties suitable for the application case since for example the doping agents also co-determine the conductivity or other electrical properties of the organic semiconductive layer under given conditions. The energetic positions of the HOMO of the matrix material and of the LUMO of the doping agent are decisive for the doping effect.

Electronic components having doped layers include OLEDS and solar cells, among others. OLEDs are known for example from U.S. Pat. No. 7,355,197 or US2009/0051271. Solar cells are known for example from US2007/0090371 and US2009/0235971.

The present invention has the task of overcoming the disadvantages of the prior art.

BRIEF SUMMARY

This task is solved by the independent claims 1 and 8 of the present application. Preferred embodiments are disclosed in the subclaims.

DESCRIPTION OF THE FIGURES

FIG. 1a Schematic diagram of a doped hole transport layer (12) on a substrate (11), wherein the hole transport layer (12) is electrically contacted by two electrodes (13) and (14). A planar structure of this kind is used as a resistor, pathway or similar.

FIG. 1b Schematic diagram of a doped hole transport layer (17) between two electrodes (16) and (18) on a substrate (15). Additional layers may also be present. Such a stacked layer structure is used for example in OLEDs, organic solar cells and the like.

Figure 1A:
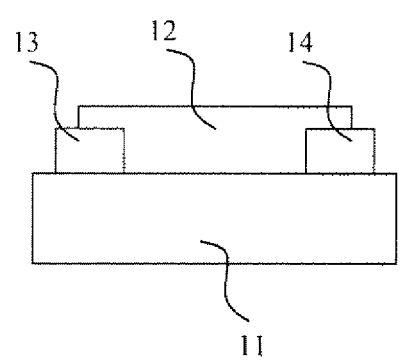
Figure 1B:
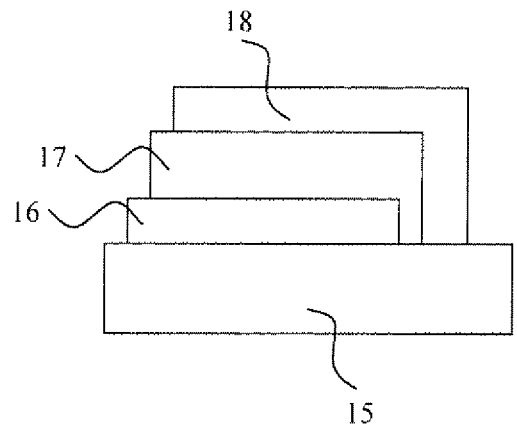

A preferred alternative of the invention provides that the following layer sequences are present in the component: (i) anode/doping agent/HTM; (ii) anode/doping agent:HTM; (iii) anode/doping agent/doping agent:HTM. The following are also preferred: (iv) doping agent/HTM/EML or (v) doping agent/HTM/OAS; (vi) p-doped HTM/EML or (vii) doping agent:WM/OAS. The p-doped HTM is doped with the doping agent according to the invention. HTM is the hole transport material; EML is the "emission layer" of an OLED; OAS stands for "optical absorption layer of a solar cell" (typically a donor-acceptor (D-A) heterotransition). "/" means that the materials occur in separate layers in a layer stack, and ":" means that the materials are present together in the same layer, the mixture may be homogeneous or not.

It is further preferred that the layer sequences (i)-(vii) are terminal layer sequences.

The recorded research into doped hole transport layers or materials for the purpose of creating these transport layers tends to focus either on the properties of the doping agent or on the properties of the hole transport material. In each case, the other component is described with generally accepted references to the related art. Indeed, it is generally possible to obtain better results for components having a doped hole transport layer than for a component with the same structure but without a doping agent in the hole transport layer. But with this narrow view of the issue one overlooks the fact that in order to fully optimise the overall properties of the component a further step is required in which the hole transport material and the doping agent are adapted with respect to one another. In particular, it must be borne in mind that the most suitable hole transport material for a doped layer is not necessary the material that functions bests as an undoped hole transport material. The doping agent and matrix rather combine to form a system that must be considered as a whole.

A key parameter for a hole transport material in an undoped layer is the "charge carrier mobility" for holes. This determines how much voltage drops across this layer when a given current density is flowing through the layer. Ideally, the charge carrier mobility is high enough to ensure that that the voltage drop across the individual layer is negligible compared with the voltage drop across the entire component. In this case, the layer no longer represents a limitation for the current flow and the charge carrier mobility may be considered to be sufficiently optimised.

In practice, this level has not yet been reached. Particularly for colourless hole transport materials that are non-absorbing in the visible spectrum, a significant voltage is required in order to drive the current flow through hole transport layers. This is even more true if the thickness of this layer cannot merely be minimal, but must be have a certain minimum layer thickness (>50 nm) for process engineering reasons or to satisfy component stability considerations, for example. In this situation, the selection of a good hole transport material for this layer must be based first and foremost on maximum hole carrier mobility in order to limit the negative consequences for the performance parameters of the component. Other parameters that describe the material, such as the glass transition temperature (Tg), processing properties, cost of manufacturing the material, are of lesser importance. For this reason, α-NPD (N,N'-di(naphthaline-1-yl)-N,N'-di(phenyl)-benzidine) with its very high hole carrier mobility is considered to be one of the best hole transport materials despite its relatively low glass transition temperature of just 96° C. Consequently, α-NPD is also used in the commercial production of OLED products even though its low glass transition temperature is a recognised disadvantage of this solution that must simply be taken into account.

The situation is different for a doped hole transport layer. The inventors have discovered that it is possible to achieve a minimal voltage drop across a doped hole transport layer for a relatively large number of hole transport materials.

Doping is typically described with reference to the energy difference between the LUMO of the doping agent and the HOMO of the HTM matrix. Because of the somewhat smaller selection of processable, very strong acceptors, certain HTMs with very low (negative.) HOMO are not good candidates for doping.

Based on the LUMO position of the 3-radialene compounds, it was considered unlikely that matrix materials with a low HOMO would lend themselves well to doping. Surprisingly, it was discovered that certain matrix materials with a low HOMO have high conductivity when they are doped with 3-radialene compounds. For a relatively large number of hole transport materials, conductivities are above the threshold value of 10−5 S/cm. With conductivity of this order, with a relatively high current density of 100 mA/cm2 voltage only falls by 0.1V across a comparatively large layer thickness of 1.00 nm. Particularly for OLED components with a typical operating voltage of at least 3 V, this value is quite minor. In this context, it is important to note that the hole transport materials that are capable of functioning in doped hole transport layers include some that exhibited poor suitability in an undoped hole transport layer and therefore have never before been used to manufacture components. It is also important to note that this phenomenon opens up new degrees of freedom in the selection of hole transport materials for doped hole transport layers.

Accordingly, the inventors set themselves the task of discovering those hole transport materials that exhibit the best possible conductivity in a doped hole transport layer, also taking into consideration the materials that were disregarded according to the conventional approach.

As a result of this research, it was found that the best combination of hole transport materials and doping agents is not that in which the doping agents are combined with the best hole transport materials. The proof of this is provided in the exemplary embodiments.

Selection of the Matrix Material

The present invention describes doping agents that are suitable for organic semiconductive materials such as hole transport materials (HT) and which are usually used in OLEDs or organic solar cells. The semiconductive materials are preferably intrinsically hole-conducting. It was found that the following materials are suitable matrix materials and can be doped with the 3-radialene compounds.

The matrix materials used were selected from compounds having the following formula (1).

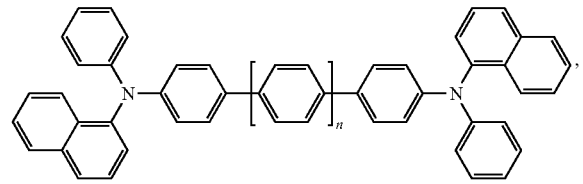

Formula (1)

in which n=1 or 2.

Compounds having formula (1) in which n=1 are preferred.

Surprisingly, it was found that a component (for example an OLED) containing compounds according to formula (1) as the doped layer has excellent operating properties compared with the prior art. This is the more surprising since the compound according to the prior art, that is to say a-NPD, has a very similar chemical structure (would be formula 1 with n=0).

Selection of the Doping Agent

Examples of acceptors are: 2,2,7,7-Tetrafluoro-2,7-dihydro-1,3,6,8-dioxa-2,7-dibora-pentachloro-benzo[e]pyrene; 1,4,5,8-Tetrahydro-1,4,5,8-tetrathia-2,3,6,7-tetracyano anthraquinone; or 1,3,4,5,7,8-Hexafluoronaphtho-2,6-quinonetetracyanomethane; 2,2'-(Perfluoronaphthalene-2,6-diylidene)dimalononitrile; 2,2'-(2,5-Dibromo-3,6-difluoro-cyclohexa-2,5-diene-1,4-diylidene)dimalononitrile; 2,2',2"-(Cyclopropane-1,2,3-triylidene)tris(2-(2,6-dichloro-3,5-difluoro-4-(trifluoromethyl)phenyl)acetonitrile); 4,4',4"-Cyclopropane-1,2,3-triylidenetris(cyanomethane-1-yl-1-ylidene)tris(2,3,5,6-tetrafluorobenzonitrile). The use of quinoids and derivatives thereof as acceptors in organic semiconductor materials is described in DE 103 57 044. Other doping agents are described in US 2008/265216. Preferred doping agents are 3-radialene compounds.

The following describes a few preferred 3-radialenes that may be used advantageously for the purposes according to the invention:

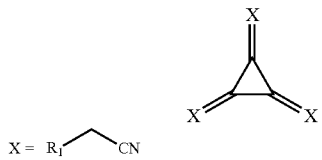

Formula (2)

wherein each $R_1$ is selected independently from the group of aryls and heteroaryls, wherein the aryl and heteroaryl are at least partially, preferably completely substituted with electron-poor groups (acceptor groups),
the aryl is preferably phenyl, biphenyl, α-naphthyl, β-naphthyl, phenantryl or anthracyl,
the heteroaryl is preferably pyridyl, pyrimidyl, triazyl or quinoxatinyl, and
the acceptor groups are electron-attracting groups, preferably selected from fluorine, chlorine, bromine, CN, trifluoromethyl or nitro.

The general synthesis of these compounds is described in patent application EP1988587 in the section entitled "Preparation of oxocarbon-, pseudooxocarbon- and radialene structures".

Additionally, doped (hole transport layers) are preferred in which the matrix material is an HTM having formula 1, where n=1 or n=2 (n=1 preferred), and the doping agent is 2,2',2''-(Cyclopropane-1,2,3-triylidene)tris(2-(p-cyanotetrafluorophenyl)acetonitrile). In the following, the HTM having formula 1 wherein n=1 will be referred to as HTM1 and the HTM having formula 1 wherein n=2 will be referred to as HTM2.

Advantages of the as described in the invention: lower absorption, improved conductivity, better thermal stability. Better overall performance compared with α-NPD.

The inventive combination of compounds having formula (1) and doping also enables flexibility in the layer structure with one doped and one undoped layer, as with one doped hole transport layer and one undoped electron blocker layer for example. The combination found enables the thicknesses of the doped and the undoped layers to be adjusted as necessary in order to optimise the component.

Electronic Component

A large number of electronic components, or devices containing such components, may be manufactured by using the organic compounds described to produce doped organic semiconductive materials, which may arranged particularly in the form or layers or electrical pathways. In particular, the material combinations according to the invention may be used in the production of organic diodes, particularly organic light emitting diodes (OLED), organic solar cells, particularly such cells with a high rectification ratio such as 103-107, preferably 104-107 or 105-107. With the doping agents used as described in the invention, it is possible to improve the conductivity of the doped layers and/or the charge carrier injection of contacts into the doped layer. Particularly with OLEDs, the component may have a pin structure or an inverted pin structure, without being limited thereto. However, the use of the material combinations according to the invention is not limited to the advantageous embodiments mentioned in the preceding. OLEDs that contain no ITO are also preferred. In addition, OLEDs having at least one organic electrode are also provided. Preferred organic electrode(s) are conductive layers that contain the following materials as primary components: PEDOT-PSS, polyaniline, carbon nanotubes, graphite.

The typical structure of a standard OLED may appear as follows:
1. Carrier, substrate, for example glass
2. Electrode, hole injecting (anode=positive terminal), preferably transparent, for example indium-tin-oxide (ITO) or FTO (Braz. J. Phys. V. 35 no. 4 pp. 1016-1019 (2005))
3. Hole injection layer,
5. Hole-side blocking layer to prevent diffusion of excitons from the emission layer and prevent charge carriers from leaking from the emission layer
6. Light-emitting layer or system of multiple layers contributing to light emission, for example CRP (carbazol derivatives) with emitter admixture (for example phosphorescent triplet emitter iridium-tris-phenylpyridine Ir(ppy)3) or Alq3 (tris-quinolinato-aluminium) mixed with emitter molecules (for example fluorescent singlet emitter coumarin),
7. Electron-side blocking layer to prevent diffusion of excitons from the emission layer and prevent charge carriers from leaking from the emission layer, for example BCP (bathocuproine),
8. Electron transport layer (ET for example BPhen, Alq3 (tris-quinolinato-aluminium).
10. Electrode, usually a metal with low work function, electron injecting (cathode=negative terminal), for example aluminium.

Of course, layers may be omitted or a layer (or a material) may fulfil multiple properties, for example layers 3-5 and/or layers 7 and 8 may be combined. Additional layers may also be inserted. Stacked OLEDs are also conceivable.

This structure describes the non-inverted (anode on the substrate), substrate-side emitting (bottom-emission) structure of an OLED. There are various concepts for describing OLEDs that emit away from the substrate (see references in DE102 15 210.1), and all of them share the feature that the substrate-side electrode (the anode in the non-inverted case) is reflective (or transparent for a transparent OLED) and the cover electrode is (semi-)transparent. If the sequence of the layers is inverted (cathode on the substrate), the OLEDs are called inverted OLEDs (see references in DE101 35 513.0). Here too, some performance may be sacrificed if specific steps are not taken.

A preferred design of the structure of an OLED according to the invention is the inverted structure (in which the cathode is on the substrate) and the light is emitted through the substrate. In addition, in one configuration it is provided that the OLED is top-emitting.

It is preferred if the hole injection layer is positioned directly adjacent to the hole-side blocking layer, in which case the hole injection layer is doped.

In any configuration of the invention, it is preferred that the hole injection layer and the hole-side blocking layer contain the same matrix material.

In a particularly preferred version of the invention, the hole-side blocking layer is at least 5 time, preferably at least 20 times thicker than the hole injection layer, in which case the hole-side blocking layer is undoped and the hole injection layer is doped.

The typical structure of an organic solar cell may appear as follows:
1. Carrier, substrate, for example glass
2. Anode, preferably transparent, for example indium-tin-oxide (ITO)
3. Hole injection layer,
5. Hole-side intermediate layer, preferably blocking layer, to prevent diffusion of exciton from the absorption layer (optically active layer, also called the emission layer) and to prevent charge carriers from leaking out of the emission layer,
6. Optically active layer (absorption layer), typically a strongly light absorbing layer from a heterotransition (two or more layers or a mixed layer) for example a mixed layer of C60 and ZnPc,
7. Electron transport layer,
10. Cathode, for example aluminium.

Of course, layers may be omitted or a layer may fulfil multiple properties. Additional layers may also be inserted.

Stacked (tandem) solar cells are intended. Variants such as transparent solar cells, inverted construction or m-i-p solar cells are also possible.

Another preferred design of the structure of a solar cell is the inverted structure (in which the cathode is on the substrate) and the light reaches the cathode through the substrate.

Further designs for solar cells are described in U.S. Pat. No. 7,675,057 B2.

Exemplary Embodiments

In the following, the invention will be explained in greater detail with reference to several exemplary embodiments.

The synthesis of the doping agents, such as F4-TCNQ and other quinoids, is known in the literature. F4-TCNQ is available commercially from the company Sigma-Aldrich Co., for example.

Synthesis of 3-Radialene Compounds

A solution 207 mmol of cyanoacetic ester in 50 ml dimethylformamide was added quickly while stirring to a solution of 207 mmol starting material (a-e) and 250 mmol potassium carbonate in 370 ml dimethylformamide. The mixture was stirred for 48 h at room temperature. Then the mixture was poured into 1 L ice water. The solution was stirred vigorously and reacted with 100 mL concentrated acetic acid. The aqueous solution was then extracted four times with chloroform. The combined organic phases were dried with magnesium sulphate and then fully concentrated in a vacuum. The raw product was used in the following synthesis without further purification.

The entire quantity of aryl cyanoacetic ester (f-j) was heated with reflux for 16 h together with 4.15 ml concentrated sulphuric acid in 84 ml acetic acid (50%). After cooling, the entire quantity was poured into 120 ml ice water and stirred for 30 min. The phases were separated and the aqueous phase was extracted with 100 ml chloroform. The combined organic phases were then washed with 100 ml water followed by 100 ml saturated sodium carbonate solution. After drying with magnesium sulphate and after the solvent was removed, the remaining substance was distilled in a vacuum to yield colourless oils (k-o).

Lithium hydride (98%) was suspended in 600 mL glyme and cooled to 0° C. 152 mmol of the aryl acetonitrile (k-o) was slowly added dropwise to 60 mL glyme. The ice bath was removed and the reaction was allowed to warm to room temperature. After 15 min stirring at room temperature the mixture was cooled to 0° C. again, and 40.0 mmol tetrachlorocyclopropene was slowly added dropwise to 40 mL glyme. The mixture was then added to 1.2 L ice water and acidified with hydrochloric acid (pH=1). The aqueous solution was extracted by shaking three times, each time with 500 mL ethyl acetate and the combined organic phases were washed first in saturated saline solution, then with water, then with sodium bicarbonate solution, and finally with water again. It was dried with magnesium sulphate and the solvent was removed in vacuum. The remaining dark brown oil was used in the following synthesis without further purification.

The material was dissolved in 1.4 L glacial acetic acid, to which a previously prepared mixture of 360 mL hydrobromic acid (48%) and 120 mL nitric acid (65%) was added dropwise while stirring. This was stirred for 1.5 h and then filtrated. The resulting red solid was washed with water, dried in a vacuum, and then purified by gradient sublimation (p-t).

| Starter material | Aryl cyanoacetic ester |
| --- | --- |
| Hexafluorobenzene (a) | (f) Ethyl-2-cyano-2-(perfluorophenyl)acetate |
| Pentafluoropyridine (b) | (g) Ethyl-2-cyano-2-(perfluoropyridin-4-yl)acetate |
| Pentafluorobenzonitrile (c) | (h) Ethyl-2-cyano-2-(4-cyanoperfluorophenyl)acetate |
| Octafluoretoluene (d) | (i) Ethyl-2-cyano-2-(4-trifluoromethylperfluorophenyl)-acetate |
| 4-Trifluoromethyl-2,6-dichloro-1,3,5-trifluorobenzene (e) | (j) Ethyl-2-cyano-2-(4-trifluoromethyl-2,6-dichloro-3,5-difluorophenyl)acetate |

| Intermediate products, Arylacetonitriles | End products, [3]-radialenes |
| --- | --- |
| (k) Pentafluorophenylacetonitrile | (p) (2E,2'E,2"E)-2,2',2"-(Cyclopropane-1,2,3-triylidene)tris(2-(perfluorophenyl)-acetonitrile) |
| (l) 4-(Cyanomethyl)-2,3,5,6-tetrafluoropyridine | (q) (2E,2'E,2"E)-2,2',2"-(Cyclopropane-1,2,3-triylidenetris(2-(perfluoropyridin-4-yl)-acetonitrile) |
| (m) 4-(Cyanomethyl)-2,3,5,6-tetrafluorobenzonitrile | (r) (2E,2'E,2"E)-2,2',2"-(Cyclopropane-1,2,3-triyliden)tris(2-(4-cyanoperfluorophenyl)-acetonitrile) |
| (n) 2-(2,3,5,6-Tetrafluoro-4-(trifluoromethyl)phenyl)-acetonitrile | (s) (2E,2'E,2"E)-2,2',2"-(Cyclopropane-1,2,3-triylidene)tris(2-(2,3,5,6-tetrafluoro-4-(trifluoromethyl)phenyl)-acetonitrile) |
| (o) (4-Trifluoromethyl-2,6-dichloro-3,5-difluorophenyl)-acetonitrile | (t) (2E,2'E,2"E)-2,2',2"-(Cyclopropane-1,2,3-triylidene)tris(2-(2,6-dichloro-3,5-difluoro-4-(trifluoromethyl)phenyl)-acetonitrile) |

Synthesis of the HTM (Hole Transport Materials)

HTM1

A 1.5 L sulphonation flask is filled with 70 g 4,4'-diiodoterphenyl, 64 g 1-naphthyl-phenylamine, 45 g potassium carbonate, 300 ml Marlotherm and 4 ml xylene. The mixture is heated to 110° C. and 20 g copper is added as a catalyst. The contents are heated to a temperature of about 195° C. within three hours. This temperature is maintained for 12 hours. Then, this stock is allowed to cool to 90° C. and drawn off via a suction filter to release inorganic components. 100 ml methanol is added and the product is drawn off in a vacuum via a suction filter. The product is then recrystallised from 2 l dimethyl formamide. After the product of recrystallisation has been drawn off it is washed again in 200 mL methanol to remove occluded dimethyl formamide.

It is dried in a drying cabinet at 100° C.

Yield: 55 g (59.06%)

Tg: 111° C.

HPLC: 98.5%

HTM2

In a 2.5 L sulphonation flask and under an argon atmosphere, a solution of 163.9 g 4-(N-1-Naphthyl-N-phenyl)-amino-4'-bromobiphenyl in 0.8 L anhydrous DMF is added dropwise to 130 g zinc, 16.8 g sodium bromide, 13 g triphenylphosphine, 12 g nickel bromide, 6 g 2,2'-bipyridine and 1 L anhydrous DMF while stirring at 70° C. The mixture is stirred for a further 2 hours at 70° C. The stock is drawn off from the zinc by suction. The solution is concentrated in a rotary evaporator, reacted with 2 L methanol, and the precipitated product is drawn off by suction. This is washed with 0.2 L methanol. The remaining substance is stirred in 0.5 L acetic acid at 100° C. and drawn off by suction after cooling. The process is repeated with 0.3 L acetic acid and then washed with 0.1 L acetic acid and 0.03 L acetone. This product is heated under reflux with 0.36 L toluene in each case and drawn off by suction after cooling. It is then dried in a drying cabinet at 70° C.

Yield: 34.6 g (25%)
HPLC: 99.3 A %
Tg: 118° C.

For use in organic semiconductors, it is preferable that both the HTMs and the doping agents have a degree of purity above 98%. To achieve this, the materials are purified repeatedly by sublimation.

Measurement Methods

The conductivity of a thin-film sample is measured using the 2-point method. In this, contacts made from a conductive material, for example gold or indium-tin-oxide, are placed on a substrate. The thin film to be examined is than deposited over a large area of the substrate, so that the contacts are completely covered by the thin film. After a voltage is applied to the contacts, the current that flows subsequently is measured. The conductivity of the thin-film material is then determined from the resistance value thus obtained on the basis of the geometry of the contacts and the film thickness of the sample. The 2-point method is permissible if the resistance of thin film is significantly greater than the resistance of the feed lines or the contact resistance. This is assured experimentally by providing a sufficiently large contact gap, and this enables the linearity of the current-voltage characteristic curve to be verified.

Thermal stability can be determined using the same method and the same structure by heating the (doped or undoped) film incrementally and measuring its conductivity after a rest period. The maximum temperature the film can sustain without losing the desired semiconductive property is then the temperature immediately before conductivity breaks down. For example, a doped film may be heated in increments of 1° C. on a substrate with two adjacent electrodes, as described above, with a waiting interval of 10 seconds between each increment. Then, conductivity is measured. The conductivity changes as the temperature changes, and above a certain temperature it breaks down suddenly. Thermal stability thus provides the temperature up to which conductivity does not abruptly break down.

Doping Concentration

The doping agent is preferably present in a doping concentration of ≤1:1 relative to the matrix molecule or the monomer unit of a polymer matrix molecule, preferably in a doping concentration of 1:2 or less, particularly preferably of 1:5 or less or 1:10 or less. The doping concentration may be restricted in a range from 1:5 to 1:10000.

The Doping Procedure

The doping of the respective matrix material with the p-doping agents to be used in accordance with the invention may be carried out in one or a combination of the following processes:

a) Mixed evaporation in the vacuum with one source for the matrix material and one for the doping agent.

b) Doping of a matrix layer by a solution of p-doping agent with subsequent evaporation of the solvent, particularly by thermal treatment c) Surface doping of a matrix material layer by a layer of doping agent applied to the surface thereof d) Preparation of a solution of matrix molecules and doping agents followed by production of a layer from this solution by conventional methods, such as vaporisation of the solvent or spin-coating In this way, it is thus possible to produce p-doped layers of organic semiconductors that lend themselves to a wide range of applications in accordance with the invention. Mixed evaporation in a vacuum (VTE) is preferred.

Conductivity Measurements

Doped Semiconductor Layer—Example 1:

A 50 nm thick layer of HTM having formula 1 was doped with compound (p). The doped layer was produced by mixed evaporation of the HTM having formula 1 and dopant (p) in a high vacuum. The concentration of the doping agent in the matrix was 10 mmol %.

For HTM1, the following results were obtained: The vaporisation temperature of the doping agent was 170° C. The vaporisation temperature of the HTM1 was 288° C. The doped layer had a high conductivity of $1.58 \cdot 10^{-4}$ S/cm. The layer had a thermal stability temperature of 110° C.

For HTM2, the following results were obtained: The vaporisation temperature of the doping agent was 163° C. The vaporisation temperature of the HTM2 was 279° C. The doped layer had a high conductivity of $2.45 \cdot 10^{-4}$ S/cm. The layer had a thermal stability temperature of 108° C.

As a comparison, the following results were obtained for n=0 (a-NPD): The vaporisation temperature of the doping agent was 172° C. The vaporisation temperature of the □-NPD was 218° C. The doped layer had a high conductivity of $6 \cdot 10^{-4}$ S/cm. The layer had a thermal stability temperature of 93° C.

Examples of Components:

A layer of HTM having formula 1 was doped with compound (p). The doped layer was deposited on a glass substrate coated with ITO by mixed evaporation of the HTM having formula 1 together with doping agent (p) in a high vacuum. The concentration of the doping agent in the matrix was 3.0% by weight. In addition, an α-NPD layer doped with 3.0% by weight of compound (p) was deposited on the same substrate as a reference. Subsequently, a layer of α-NPD, a fluorescent blue emitter layer, an undoped ETL and blocking layer, an electron transport layer mixed with LiQ and an aluminium cathode were deposited without breaking the vacuum. The components processed in this way were then protected from water by encapsulating in a covering glass—an appropriate getter had been introduced in advance. In all, 3 samples were prepared, with HTM1, HTM2 and a-NPD instead of HTM with formula 1.

Figure 2:
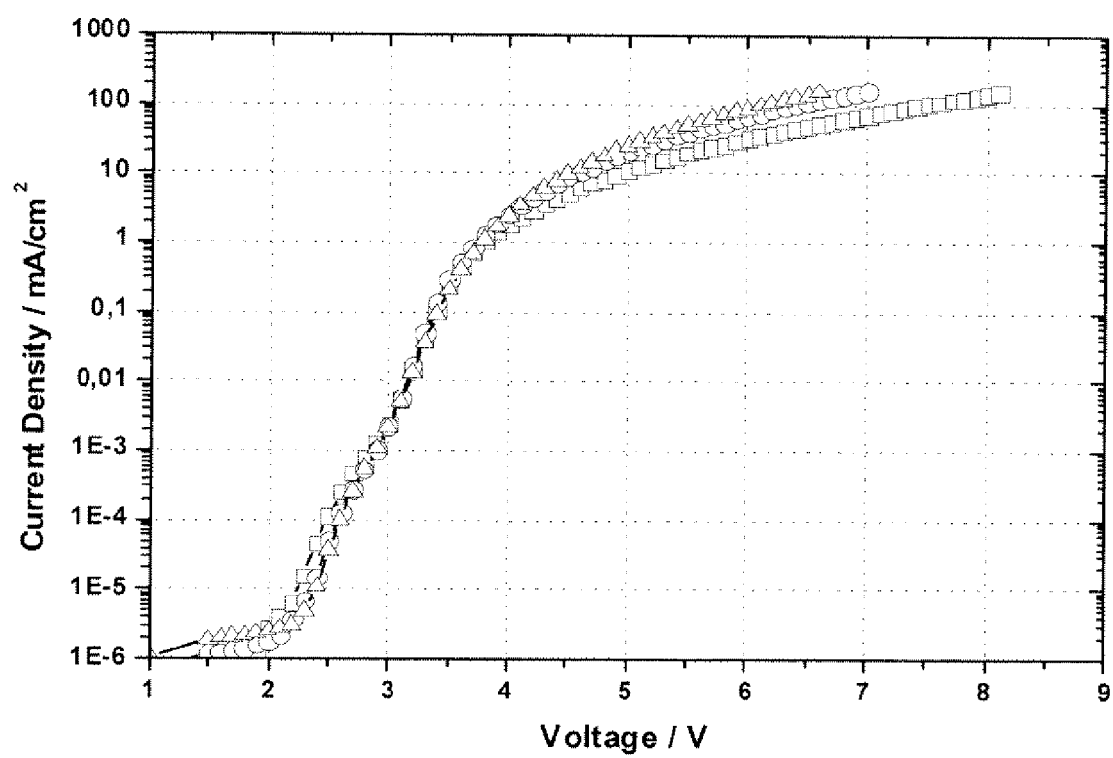
FIG. 2 Comparison of the diode characteristic curves for two OLEDs according to the invention and one according to the prior art.

In this way, blue OLEDs are produced that emit through the glass substrate and whose characteristic data is compared in FIG. 2. In FIG. 2, the data from HTM1 is indicated by circles, the data from HTM2 by triangles, and the data from a-NPD by rectangles. A significant advantage is detectable for both HTM1 and HTM2 (the current scale is logarithmic).

Figure 3:
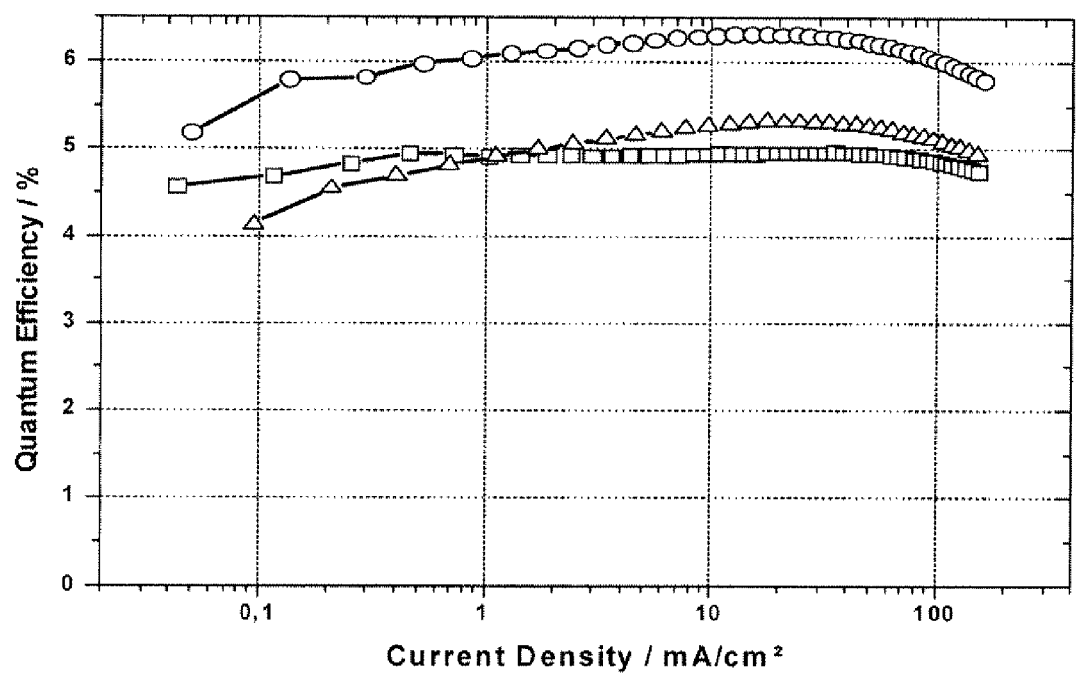
FIG. 3 Quantum efficiency versus current density of the OLEDs used in FIG. 2.

FIG. 3 shows the quantum efficiency of the three light emitting diodes. It is evident that the OLED with a-NPD performs less well than the others. The performance of HTM1 is also superior to that of HTM2. The emission spectra are identical in shape, thus again confirming the comparability of the data.

Figure 4:
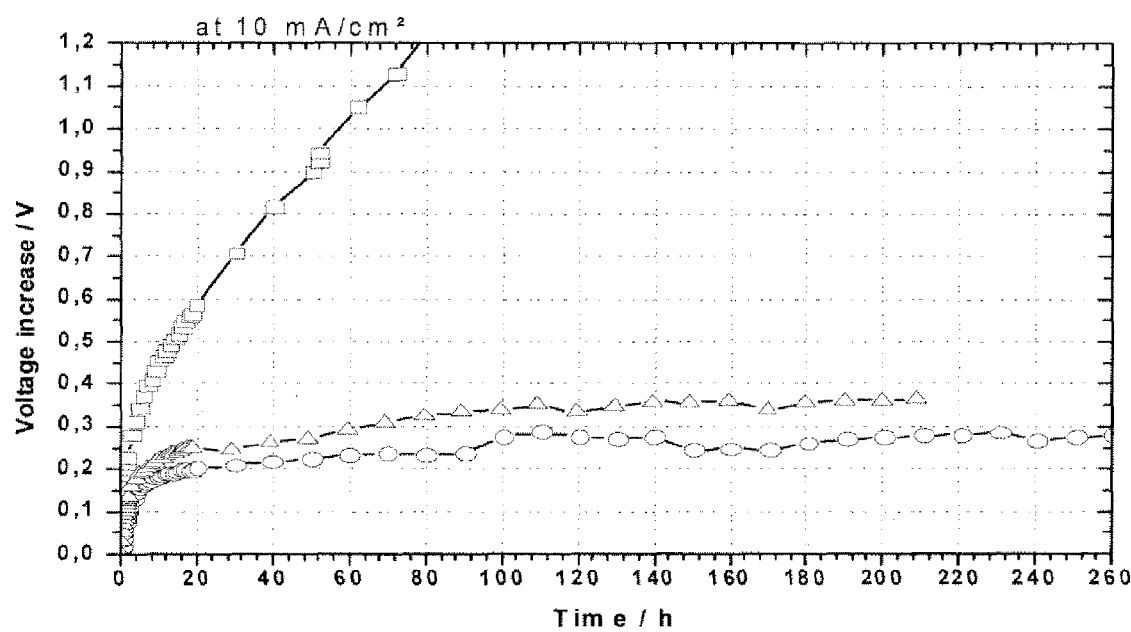
FIG. 4 Long-term measurement of the diodes used in constant current operation.

FIG. 4 shows the chronological progression of the operating voltage for a constant operating current of 10 mA/cm^2. It is detectable that HTM1 and HTM2 manifest a smaller voltage increase than □-NPD.

In this description, a doping agent that is used to dope an HTM (hole transport material) is an electrical p-doping agent. This means that a classic chemical reaction creating a chemical bond does not take place between the doping agent and the HTM. The doping agents are preferably neutral species. Neutral precursor species may also be used. The doping agents are preferably organic compounds.

The term matrix refers to the material that constitutes at least 50 mol %, and preferably more than 50 mol % of the layer.

The features of the invention disclosed in the preceding description, the claims and the drawing may be essential both individually and in any combination to the realisation of the invention in its various embodiments.

The invention claimed is:

1. An organic semiconductive material comprising at least one matrix material and at least one electrical doping material, wherein the matrix material is selected from compounds having formula (1):

Formula (1)

wherein n is 1 or 2.

2. The organic semiconductive material as recited in claim 1, wherein the electrical doping material has a LUMO equal to or more positive than 0.0 V.

3. The organic semiconductive material as recited in claim 1, wherein the electrical doping material is selected from compounds having formula (2):

Formula (2)

wherein X is $R_1$ CN, wherein each $R_1$ is selected independently from the group consisting of aryl and heteroaryl, wherein the aryl and heteroaryl are at least partially substituted with electron-poor groups (acceptor groups), wherein the acceptor groups are electron-attracting groups.

4. The organic semiconductive material as recited in claim 1, wherein the electrical doping material is embedded in the matrix material.

5. The organic semiconductive material as recited in claim 1, wherein the electrical doping material and the matrix material comprise two layers that are in physical contact with one another.

6. The organic semiconductive material as recited in claim 1, wherein the matrix material is present in a first and a second layer, wherein either the first or the second layer is doped with the electrical doping material.

7. The organic semiconductive material as recited in claim 1, wherein the electrical doping material is selected from:
2,2',2''-(Cyclopropane-1,2,3-triylidene)tris(2-(perfluorophenyl)-acetonitrile);
2,2',2''-(Cyclopropane-1,2,3-triylidene)tris(2-(perfluoropyridin-4-yl)-acetonitrile);
2,2',2''-(Cyclopropane-1,2,3-triylidene)tris(2-(4-cyanoperfluorophenyl)-acetonitrile);
2,2',2''-(Cyclopropane-1,2,3-triylidene)tris(2-(2,3,5,6-tetrafluoro-4-(trifluoromethyl)phenyl)-acetonitrile); or
(Cyclopropane-1,2,3-triylidene)tris(2-(2,6-dichloro-3,5-difluoro-4-(trifluoromethyl)phenyl)-acetonitrile).

8. An organic component comprising an organic semiconductive material, wherein the organic semiconductive material comprises at least one matrix material and at least one electrical doping material, wherein the matrix material is selected from compounds having formula (1):

Formula (1)

wherein n is 1 or 2.

9. The organic component as recited in claim 8, wherein the organic component is a light emitting component.

10. The organic component as recited in claim 8, wherein the organic component is an organic solar cell.

11. The organic semiconductive material as recited in claim 2, wherein the electrical doping material has a LUMO equal to or more positive than 0.24 V in MeCN vs Fc/Fc+.

12. The organic semiconductive material as recited in claim 3, wherein the aryl and heteroaryl are completely substituted with electron-poor groups (acceptor groups).

13. The organic semiconductive material as recited in claim 3, wherein the aryl is independently selected from phenyl, biphenyl, α-naphthyl, β-naphthyl, phenantryl, or anthracyl.

14. The organic semiconductive material as recited in claim 3, wherein the heteroaryl is independently selected from pyridyl, pyrimidyl, triazyl, or quinoxalinyl.

15. The organic semiconductive material as recited in claim 3, wherein the acceptor groups are independently selected from fluorine, chlorine, bromine, CN, trifluoromethyl, or nitro.

16. The organic semiconductive material as recited in claim 1, wherein the first and second layers are arranged adjacent to one another.

* * * * *